(12) United States Patent
Long et al.

(10) Patent No.: US 11,877,912 B2
(45) Date of Patent: Jan. 23, 2024

(54) SYSTEMS AND METHODS FOR COUPLING A WEARABLE THERAPY SYSTEM TO A DRESSING

(71) Applicant: KCI LICENSING, INC., San Antonio, TX (US)

(72) Inventors: Justin Alexander Long, San Antonio, TX (US); Christopher Brian Locke, Blandford Forum (GB); Richard Coulthard, San Antonio, TX (US)

(73) Assignee: 3M Innovative Properties Company, Saint Paul, MN (US)

( * ) Notice: Subject to any disclaimer, the term of this patent is extended or adjusted under 35 U.S.C. 154(b) by 751 days.

(21) Appl. No.: 15/733,332

(22) PCT Filed: Jan. 3, 2019

(86) PCT No.: PCT/US2019/012122
§ 371 (c)(1),
(2) Date: Jun. 29, 2020

(87) PCT Pub. No.: WO2019/139806
PCT Pub. Date: Jul. 18, 2019

(65) Prior Publication Data
US 2020/0337908 A1    Oct. 29, 2020

Related U.S. Application Data

(60) Provisional application No. 62/615,035, filed on Jan. 9, 2018.

(51) Int. Cl.
*A61F 13/02* (2006.01)
*A61B 46/20* (2016.01)
(Continued)

(52) U.S. Cl.
CPC .......... *A61F 13/0266* (2013.01); *A61B 46/20* (2016.02); *A61F 13/0206* (2013.01);
(Continued)

(58) Field of Classification Search
CPC .............. A61F 13/0216; A61F 13/0266; A61F 13/0269; A61F 13/0253; A61F 2013/00289
See application file for complete search history.

(56) References Cited

U.S. PATENT DOCUMENTS 8,163,003 B2 * 4/2012 Boyden .................... A61F 2/02
623/1.13
2006/0289113 A1 12/2006 Cura et al.
(Continued)

FOREIGN PATENT DOCUMENTS

EP        2371920        10/2011
WO    WO 2000/061692    10/2000
(Continued)

OTHER PUBLICATIONS

International Search Report and Written Opinion issued in corresponding PCT Application No. PCT/US2019/012122, dated Oct. 4, 2019.

*Primary Examiner* — Camtu T Nguyen

(57) ABSTRACT

Provided herein is a system and method for coupling a wearable therapy system to a dressing and detaching the wearable therapy system from the dressing. One aspect provides a system including a drape with a switchable adhesive layer and a therapy system adhered to the drape via the switchable adhesive layer. The therapy system includes one or more radiation sources that can emit radiation wavelengths (e.g., light or electromagnetic waves) to impinge upon the adhesive and deactivate the adhesive when it is desired to remove the therapy system from the drape.

19 Claims, 5 Drawing Sheets

(51) Int. Cl.
*A61M 1/00* (2006.01)
*A61F 13/00* (2006.01)

(52) U.S. Cl.
CPC ...... *A61F 13/0216* (2013.01); *A61F 13/0253* (2013.01); *A61F 13/0269* (2013.01); *A61M 1/90* (2021.05); *A61B 2046/205* (2016.02); *A61F 2013/00289* (2013.01); *A61M 2205/75* (2013.01)

(56) References Cited

U.S. PATENT DOCUMENTS

2009/0204084 A1\* 8/2009 Blott ................ A61M 3/022
604/290
2009/0216170 A1\* 8/2009 Robinson ........... A61F 13/0246
602/60

FOREIGN PATENT DOCUMENTS

WO    WO 2017/091515     6/2017
WO    WO 2017/151226     9/2017
WO    WO 2017/151226 A1 \* 9/2017

\* cited by examiner

SYSTEMS AND METHODS FOR COUPLING A WEARABLE THERAPY SYSTEM TO A DRESSING

CROSS-REFERENCE TO RELATED APPLICATIONS

This application is a national phase application under 35 U.S.C. § 371 of International Application No. PCT/US2019/012122, filed Jan. 3, 2019, which claims priority to and the benefit of U.S. Provisional Application No. 62/615,035, filed Jan. 9, 2018. The contents of the referenced patent applications are incorporated into the present application in their entirety.

BACKGROUND

1. Field of Invention

The present application relates generally to the field of tissue treatment, and more specifically to a system and method for coupling a wearable therapy system to a dressing and detaching the wearable therapy system from the dressing.

2. Description of Related Art

Systems and devices currently exist for the treatment of tissue, such as wound tissue and skin tissue. Some current tissue treatment systems require the use of an adhesive drape or dressing to secure all or a portion of the tissue treatment system to a tissue site. For example, an adhesive drape can be used to secure a gauze portion of a bandage to a wound site by adhering to the skin or other tissue surrounding the wound. Wearable negative pressure wound therapy (NPWT) and fluid management systems need to be securely attached to the dressing covering the wound that is being treated. This connection needs to provide both a means to fix these two subsystems together and a leak free seal to ensure wound fluids are not lost and that a therapeutic pressure can be maintained. Traditional means to do this include rigid couplings that snap or screw together or that use an adhesive to bond the components. While both of these can provide the required coupling, they have their own disadvantages. For instance, a rigid coupling requires relatively costly components to be manufactured and, when in place, add to the bulk above the wound site. An adhesive solution is low profile and cheaper but a bond that is strong enough to be useful in practice will mean that the parts cannot be easily separated later if the dressing or therapy unit needs to be changed. The challenge with such adhesive couplings is separating them when the dressing needs to be changed such that there is no damage to either the treatment unit or the tissue site, particularly important if considering connection to a 7-day wearable fluid storage and negative pressure system.

SUMMARY

To alleviate the existing problems described above, the disclosed embodiments describe a system and method for coupling a wearable therapy system to a dressing and detaching the wearable therapy system from the dressing. In some embodiments, a radiation deactivated adhesive drape has an inner surface configured to be coupled to tissue and an outer non-tissue facing surface. The drape may include a switchable adhesive disposed on the outer drape surface, the switchable adhesive being configured to adhere the drape to a medical therapy unit, the switchable adhesive including: a radiation-sensitive adhesive layer having at least one release agent disposed within the adhesive layer, wherein the at least one release agent is configured to weaken a bond of the adhesive layer to a surface upon exposure to at least one of a plurality of radiation wavelengths; and a removable blocking layer having at least one blocking agent disposed within the blocking layer, wherein the blocking layer blocks the at least one of a plurality of radiation wavelengths from exposing the photosensitive adhesive layer. In some embodiments, the plurality of radiation wavelengths are a plurality of light wavelengths. In some embodiments, the plurality of light wavelengths include ultraviolet (UV) light wavelengths. In some embodiments, the plurality of light wavelengths are between 280 nm and 400 nm. In some embodiments, the plurality of light wavelengths are between 320 nm and 370 nm. In some embodiments, the at least one release agent is a photo initiator configured to deactivate the adhesive layer upon exposure to the at least one of a plurality of light wavelengths. In some embodiments, the plurality of radiation wavelengths are a plurality of electromagnetic wavelengths. In some embodiments, the plurality of electromagnetic wavelengths include radio-frequency wavelengths. In some embodiments, the plurality of electromagnetic wavelengths include microwaves. In some embodiments, the at least one release agent is a nanoferrite configured to deactivate the adhesive layer upon exposure to the at least one of a plurality of electromagnetic wavelengths. In some embodiments, the nanoferrite is an iron oxide particle that is super-paramagnetic. In some embodiments, the nanoferrite has a particle size of less than 30 nm. In some embodiments, the removable blocking layer is disposed on an outer surface of the photosensitive adhesive layer. In some embodiments, the removable blocking layer is a peelable layer that covers the adhesive layer. In some embodiments, the drape further comprises a filter layer configured to block at least a portion of the at least one of the plurality of radiation wavelengths that activate the at least one release agent. In some embodiments, the blocked portion of the at least one of the plurality of radiation wavelengths comprises one or more wavelengths below a wavelength intensity threshold. In some embodiments, the drape further comprises an aperture disposed through the drape configured to receive a portion of the medical therapy unit, wherein the switchable adhesive is disposed on the outer drape surface as an adhesive ring surrounding the aperture.

In some embodiments, a medical therapy unit for medical fluid collection for attachment to a radiation deactivated adhesive drape includes: an adhesive layer receiving area disposed on an outside surface of the medical therapy unit configured to allow a passage of at least one of a plurality of radiation wavelengths through the adhesive layer receiving area; a radiation source disposed within the medical therapy unit adjacent to the adhesive layer receiving area and configured to emit the at least one of a plurality of radiation wavelengths; and a radiation source controller having at least one processor configured to control an ON/OFF state of the radiation source. In some embodiments, the radiation source is a light source and the at least one of a plurality of radiation wavelengths are a plurality of light wavelengths. In some embodiments, the light source is an ultraviolet (UV) light source and the at least one of a plurality of light wavelengths are UV light wavelengths. In some embodiments, the plurality of light wavelengths are between 285 nm and 400 nm. In some embodiments, the plurality of light wavelengths are between 320 nm and 370 nm. In some embodiments, the light source comprises one or more UV light emitting diodes (LEDs). In some embodiments, the medical therapy unit further comprises a light diffuser disposed between the light source and the adhesive layer receiving area and configured to focus the at least one of a plurality of light wavelengths to pass through the adhesive layer receiving area. In some embodiments, the radiation source is an electromagnetic radiation source and the plurality of radiation wavelengths are a plurality of electromagnetic wavelengths. In some embodiments, the plurality of electromagnetic wavelengths include radio-frequency wavelengths. In some embodiments, the plurality of electromagnetic wavelengths include microwaves. In some embodiments, the radiation source controller is configured to receive a radiation source activation signal and output an ON signal. In some embodiments, the medical therapy unit further comprises a radiation source driver configured to receive the ON signal from the radiation source controller and turn the radiation source to an ON state. In some embodiments, the adhesive layer receiving area is configured to receive a switchable adhesive including a radiation-sensitive adhesive layer having at least one release agent disposed within the adhesive layer, wherein the at least one release agent is configured to weaken a bond of the adhesive layer to a surface upon exposure to the at least one of the plurality of radiation wavelengths. In some embodiments, the medical therapy unit further comprises: a negative pressure generation unit configured to transmit one or more gasses within the medical therapy unit; a flexible pouch having a first end coupled to the negative pressure generation unit and a second end coupled to the adhesive layer receiving area, wherein the flexible pouch is configured to enable passage of the one or more gasses and absorb and/or wick wound fluids; and a filter disposed at the second end of the flexible pouch.

In some embodiments, a medical fluid collection system comprises: a medical therapy unit including: an adhesive layer receiving area disposed on an outside surface of the medical therapy unit configured to allow a passage of at least one of a plurality of radiation wavelengths through the adhesive layer receiving area; a radiation source disposed within the medical therapy unit adjacent to the adhesive layer receiving area and configured to emit the at least one of a plurality of radiation wavelengths; and a radiation source controller having at least one processor configured to control an ON/OFF state of the radiation source; and a drape having an inner surface configured to be coupled to tissue and an outer non-tissue facing surface, the drape including: a switchable adhesive disposed on the outer drape surface, the switchable adhesive being configured to adhere the drape to the medical therapy unit, the switchable adhesive including: a radiation-sensitive adhesive layer having at least one release agent disposed within the adhesive layer, wherein the at least one release agent is configured to weaken a bond of the adhesive layer to a surface upon exposure to the at least one of the plurality of radiation wavelengths; and a removable blocking layer having at least one blocking agent disposed within the blocking layer, wherein the blocking layer blocks the at least one of a plurality of radiation wavelengths from exposing the photosensitive adhesive layer, wherein the medical therapy unit is coupled to the drape via the switchable adhesive adhering the outer drape surface to the adhesive receiving area. In some embodiments, the radiation source is a light source and the at least one of a plurality of radiation wavelengths are a plurality of light wavelengths. In some embodiments, the light source is an ultraviolet (UV) light source and the at least one of a plurality of light wavelengths are UV light wavelengths. In some embodiments, the plurality of light wavelengths are between 285 nm and 400 nm. In some embodiments, the plurality of light wavelengths are between 320 nm and 370 nm. In some embodiments, the light source comprises one or more UV light emitting diodes (LEDs). In some embodiments, the system further comprises a light diffuser disposed between the light source and the adhesive layer receiving area and configured to focus the at least one of a plurality of light wavelengths to pass through the adhesive layer receiving area. In some embodiments, the radiation source is an electromagnetic radiation source and the plurality of radiation wavelengths are a plurality of electromagnetic wavelengths. In some embodiments, the plurality of electromagnetic wavelengths include radio-frequency wavelengths. In some embodiments, the plurality of electromagnetic wavelengths include microwaves. In some embodiments, the radiation source controller is configured to receive a radiation source activation signal and output an ON signal. In some embodiments, the system further comprises a radiation source driver configured to receive the ON signal from the radiation source controller and turn the radiation source to an ON state. In some embodiments, the medical therapy unit is configured to detach from the drape upon exposure of the switchable adhesive to the at least one of a plurality of radiation wavelengths emitted from the radiation source. In some embodiments, the medical therapy unit is coupled to the drape in a leak-proof connection.

In some embodiments, a method of operating a medical fluid collection system comprises: adhering a medical therapy unit to a drape having an inner surface configured to be coupled to tissue and an outer non-tissue facing surface, the adhering including: removing a removable blocking layer from a radiation-sensitive adhesive layer disposed on the outer surface of the drape; and attaching the adhesive layer to an adhesive layer receiving area disposed on an outside surface of the medical therapy unit; and detaching the medical therapy unit from the drape, the detaching including: activating a radiation source disposed within the medical therapy unit adjacent to the adhesive layer receiving area and configured to emit at least one of a plurality of radiation wavelengths; exposing the radiation-sensitive adhesive layer to at least one of the plurality of radiation wavelengths, wherein the radiation-sensitive adhesive layer is deactivated upon exposure to the at least one of a plurality of radiation wavelengths; and removing the medical therapy unit from the drape.

BRIEF DESCRIPTION OF THE DRAWINGS

Those of skill in the art will understand that the drawings, described below, are for illustrative purposes only. The drawings are not intended to limit the scope of the present teachings in any way.

DETAILED DESCRIPTION

Figure 1A:
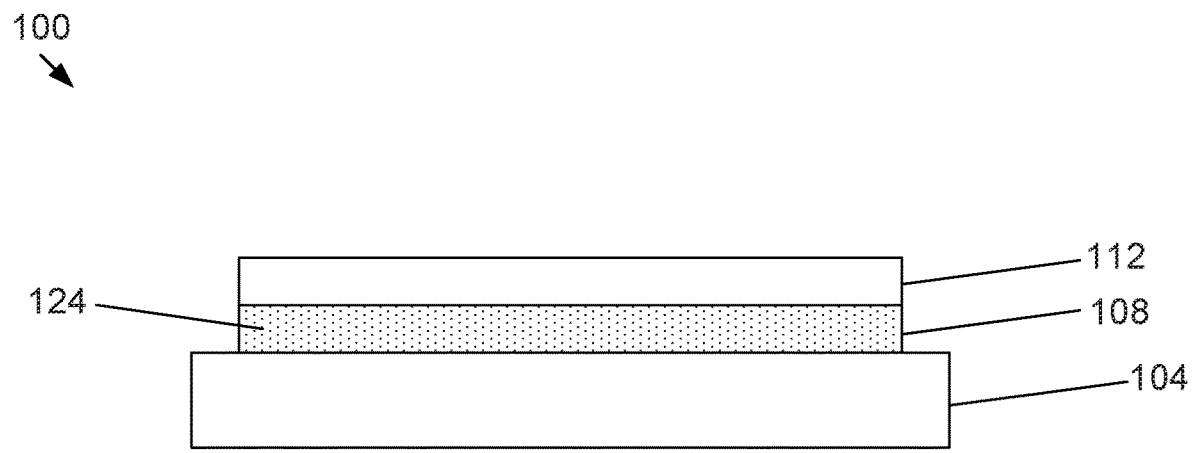
FIGS. 1A-1D are cross-sectional views of a light deactivated (switchable) adhesive system in accordance with an illustrative embodiment of the present disclosure.

In the following detailed description of the preferred embodiments, reference is made to the accompanying drawings that form a part hereof, and in which is shown by way of illustration specific preferred embodiments in which the invention can be practiced. These embodiments are described in sufficient detail to enable those skilled in the art to practice the invention, and it is understood that other embodiments can be utilized and that logical structural, mechanical, electrical, and chemical changes can be made without departing from the spirit or scope of the invention. To avoid detail not necessary to enable those skilled in the art to practice the invention, the description can omit certain information known to those skilled in the art. It is understood that reference to a feature by numeric designation does not necessarily refer only to any particular embodiment depicted in a drawing. The following detailed description is, therefore, not to be taken in a limiting sense, and the scope of the present invention is defined only by the appended claims.

The following definitions are provided to better define the present invention and to guide those of ordinary skill in the art in the practice of the present invention. Unless otherwise noted, terms are to be understood according to conventional usage by those of ordinary skill in the relevant art.

Reduced pressure generally refers to a pressure less than the ambient pressure at a tissue site that is being subjected to treatment. In most cases, this reduced pressure will be less than the atmospheric pressure of the location at which the patient is located. Although the terms "vacuum" and "negative pressure" can be used to describe the pressure applied to the tissue site, the actual pressure applied to the tissue site can be significantly less than the pressure normally associated with a complete vacuum. Consistent with this nomenclature, an increase in reduced pressure or vacuum pressure refers to a relative reduction of absolute pressure, while a decrease in reduced pressure or vacuum pressure refers to a relative increase of absolute pressure.

As used herein, the term "coupled" includes "indirect coupling" via a separate object. For example, a drape can be coupled to the tissue site if both the drape and the tissue site are coupled to one or more third objects, such as a release agent or a second adhesive layer. The term "coupled" also includes "directly coupled," in which case the two objects touch each other in some way. The term "coupled" also encompasses two or more components that are continuous with one another by virtue of each of the components being formed from the same piece of material. Also, the term "coupled" includes chemical coupling, such as via a chemical bond, and electrostatic coupling.

Various aspects of the present invention comprise a system and method for coupling a wearable therapy system to a dressing and detaching the wearable therapy system from the dressing, exemplary embodiments of which are shown in FIGS. 1A-4. Specifically, the embodiments described herein have a fluid management and therapy system to manage wound fluids which is attached to a wound dressing by an adhesive. The adhesive used is "switchable" or light deactivated by exposure to light at a specific wavelength (e.g., UVA, UVB, UVC) or electromagnetic radiation at specific frequency or wavelength (e.g., radio frequency waves). All wavelengths which are usable for crosslinking/heating, in particular radiofrequency waves, ultraviolet waves, and microwaves, can be useful for deactivating the switchable adhesive. In a switchable adhesive, the level of adhesion can be altered so that a strong bond is provided during the phase where the components need to be securely sealed and fixed together but when removal is required, a light source with the correct wavelength or a chemical reaction can be applied to the adhesive. The wavelengths significantly crosslinks the polymer chain of the adhesive so that it moves from being in a viscoelastic state to an elastic state, thus reducing the adhesion level so the adhesive can be easily removed. The therapy/fluid management system has the means to initiate this reaction on command from a user (e.g., by activating a light source or starting a chemically initiated reaction). In order to prevent premature switching, the adhesive is protected from exposure to the activating energy. This can be achieved by physical shielding or filtering or by choosing a deactivating frequency that is not strong in ambient conditions. For example, the absorbent and wicking structure of the dressing and drape layers may be able to provide physical shielding. However, the shielding may also be provided by selecting a wavelength of light in the ultraviolet portion of the spectrum that is not normally present in ambient light (e.g., UVB or UVC).

Referring more specifically to the drawings, FIGS. 1A-1D show cross-sectional views of a light deactivated (switchable) adhesive system 100 in accordance with an illustrative embodiment of the present disclosure. As shown in FIG. 1A, the system 100 comprises a surface 104, a photosensitive adhesive layer 108, and a blocking layer 112. In the embodiment shown, adhesive layer 108 is affixed to the surface 104 on one side of the adhesive layer and coupled to blocking layer 112 on a side opposite the side affixed to surface 104. In the embodiment shown, surface 104 is an outside surface of a dressing or drape. In the embodiment shown, the adhesive layer 108 may cover any portion of the surface 104 as may be required to securely affix the dressing to the medical therapy unit. The adhesive layer 108 can comprise any material, in single or multiple layers, capable of adhering to surface 104.

Figure 1B:
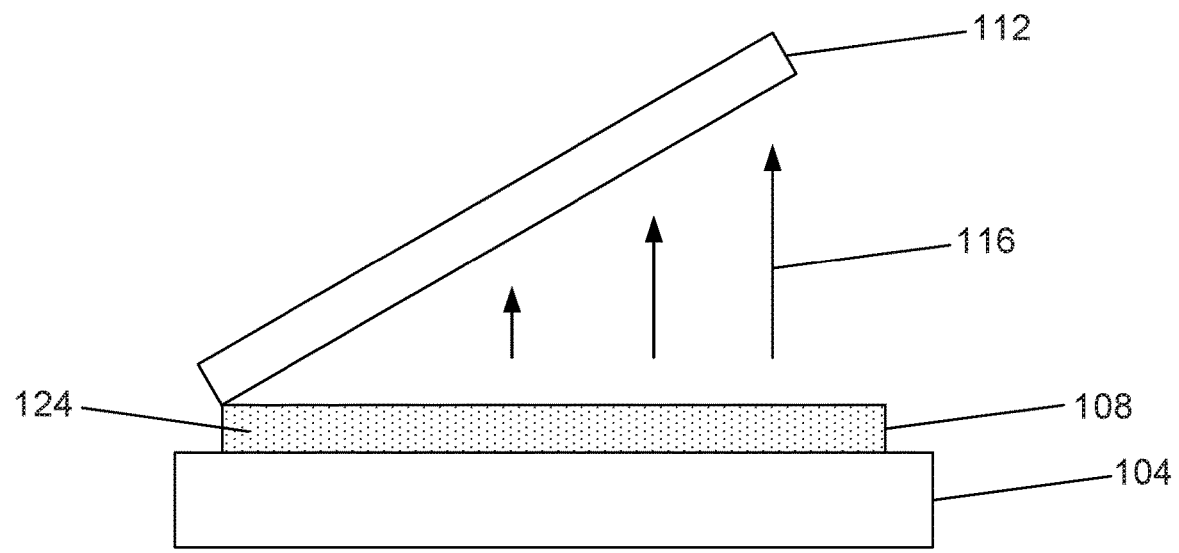
Figure 1C:
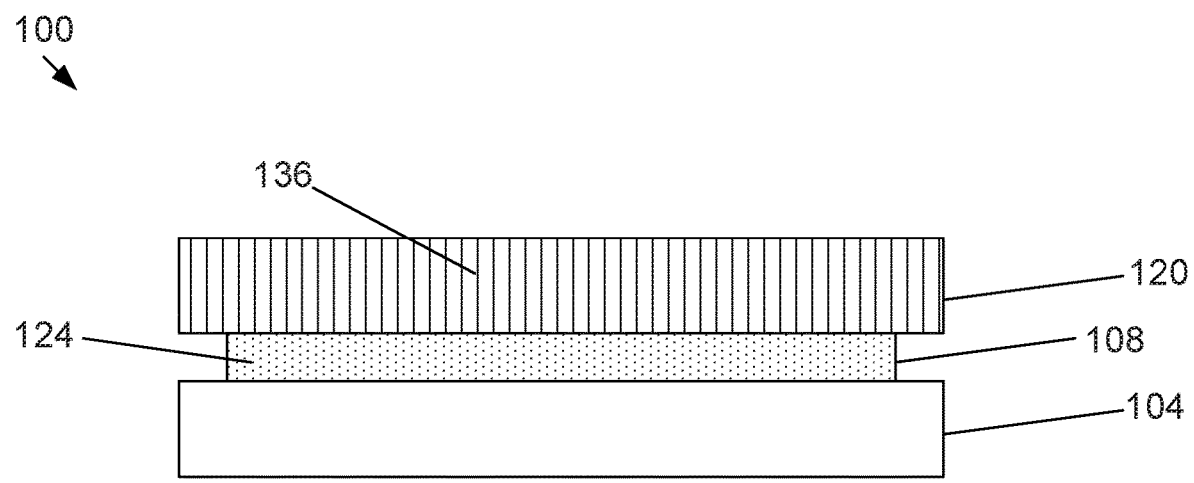

In the embodiment shown, prior to attaching the medical therapy unit to the dressing, the adhesive layer 108 is covered by blocking layer 112. Blocking layer 112 is a removable layer that covers the adhesive surface of the adhesive layer 108 until the adhesive layer is desired to be adhered to another surface such as an adhesive receiving surface of the medical therapy unit. As shown in FIG. 1B, the blocking layer 112 can be peeled off or otherwise removed with a force (represented by arrows 116) to expose an adhesive surface of adhesive layer 108 before applying the adhesive surface to a surface 120 (as shown in FIG. 1C). The adhesive layer 108 can comprise one or more materials including, but not limited to, polyurethane, acrylic (e.g., cyanoacrylate), hydrogel, silicon or silicone based material, natural rubber, synthetic rubber, styrene block copolymers, polyvinyl ethers, poly(meth)acrylates, polyolefins, hydrocolloid (e.g., a rubber based hydrocolloid), or a combination thereof. In some embodiments, the adhesive layer 108 comprises a polymer or co-polymer. For example, the adhesive layer 108 can comprise a co-polymer of polyurethane and silicone or various acrylic co-polymers.

In the embodiment shown in FIG. 1A, the adhesive layer 108 may include at least one release agent 124 comprising a release material. In the embodiment shown, adhesive layer 108 has a plurality of release agents 124 (represented by dots). The release agent 124 can physically or chemically affect adhesion characteristics of adhesive layer 108. A release agent 124 can comprise a variety of molecular compositions depending on the particular embodiment being implemented, including but not limited to a photopolymer, an oil particle, a gas particle, a solvent, a lipid, and/or one or more microstructures. Release agents 124 can be present in an inert or inactive form in, on, or near an adhesive layer 108. For example, a release agent 124 can be mixed with the adhesive; on the surface of the adhesive with a random or patterned coverage; coupled to the drape with a random or patterned coverage; or contained within a microstructure located in these or other locations. Upon release or activation, release agents 124 can migrate within the adhesive layer 108 or along an interface between an adhesive layer 108 and surface 120 to facilitate the removal of a canister (e.g., surface 104) from the medical therapy unit (e.g., surface 120). In the embodiment shown, the release agent 124 is configured to transition from an unreleased state (shown in FIG. 1A) to a release state 128 (represented by diagonal lines in FIG. 1D) to weaken a bond of the adhesive layer 108 to surface 120 upon exposure to an external stimulus. Various external stimulus can be employed depending on the particular embodiment being implemented. Non-limiting examples of the external stimulus include electromagnetic (e.g., UV, visible, or infrared light), magnetic, sound, pH, pressure (e.g., positive atmospheric pressure, negative atmospheric pressure, shear force, direct force), thermal, moisture, or a substance. The external stimulus can also be a substance, compound, liquid, or gas capable of reacting with a release agent 124 in adhesive layer 108 such that the release agent 124 transitions from an unreleased state to a released state. In the embodiment shown, the external stimulus is one or more of a plurality of light wavelengths. The weakened bond that occurs as a result of the release of release agent 124 allows a user of the system 100 to apply a force on surface 104, such as a force indicated by arrow 132, to remove adhesive layer 108 from tissue 120.

Referring more specifically to FIG. 1A, in the embodiment shown, release agents 124 are inertly dispersed within adhesive layer 108 and can be located anywhere within adhesive layer 108, as well as any of the outer surfaces of adhesive layer 108, such as an interface between adhesive layer 108 and blocking layer 112. In some embodiments, a separate film layer (not shown in FIG. 1A), can separate release agents 124 from adhesive layer 108. In these embodiments, the presence of an external stimulus can weaken, break-down, or increase the permeability of the separate film layer such that release agents 124 are allowed to migrate into adhesive layer 108 to facilitate the removal of adhesive layer 108 from surface 120.

Figure 1D:
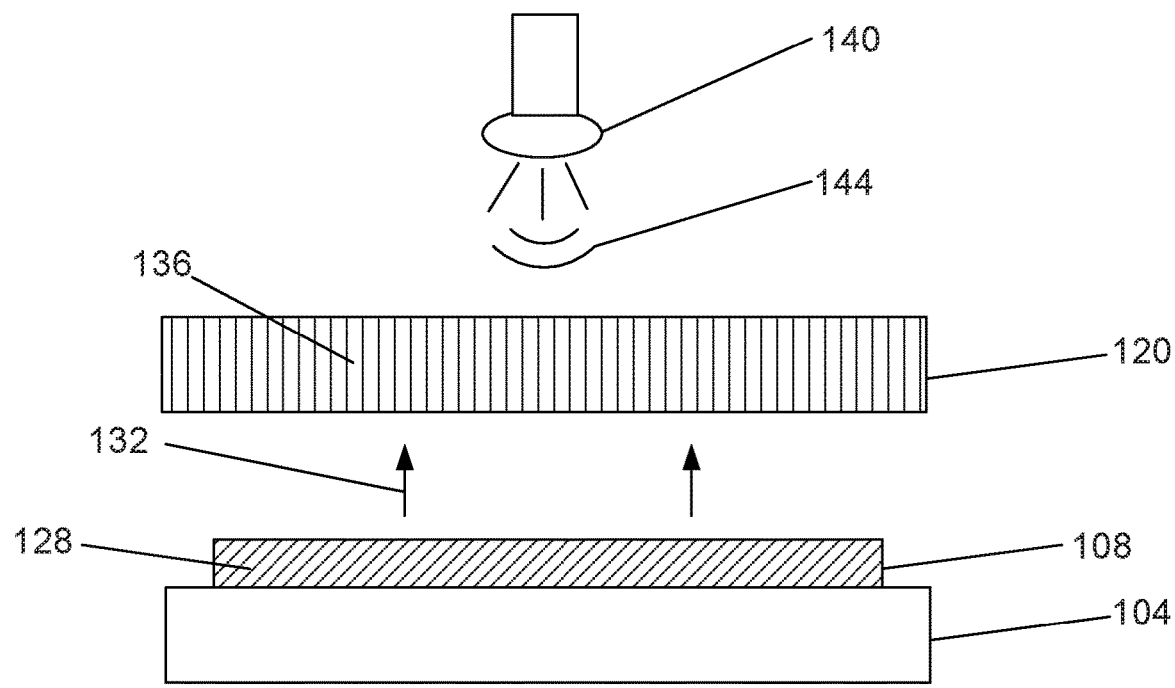

As shown in FIG. 1B, blocking layer 112 is removed from the adhesive surface of adhesive layer 108 via force 116. This exposes the adhesive surface of adhesive layer 108 and enables it to adhere to surface 120, as shown in FIG. 1C. In some embodiments, blocking layer 112 is a removable label or protective cover disposed on the adhesive surface of adhesive layer 108 that can be peeled off or otherwise removed from the surface of adhesive layer 108. In the embodiment shown, surface 120 has various apertures or passageways (denoted by lines 136) that allow certain wavelengths of light to pass through surface 120. As shown in FIG. 1D, release agents 124 may be released in the presence of external stimulus such that release agents 124 are allowed to migrate within adhesive layer 108 and the interface between adhesive layer 108 and tissue 120. In the embodiment shown, a UV light source 140 emits a plurality of light wavelengths 144 that pass through passageways 136 and expose adhesive layer 108 to the plurality of light wavelengths 144. In some embodiments, exposure to the plurality of light wavelengths 144 can cause microstructures containing release agents 124 to rupture or tear, thereby releasing release agents 124 from the interior of the microstructures. These released release agents 124 can then be interspersed into adhesive layer 108 and the interface between adhesive layer 108 and surface 120, thereby weakening the bond between adhesive layer 108 and surface 120 and facilitating the removal of adhesive layer 108 from surface 120. As the plurality of light wavelengths 144 reach adhesive 108, release agents 124 may transition from an unreleased state (as shown in FIG. 1A) to a released state 128 (as shown in FIG. 1D) as they are exposed to the plurality of light wavelengths 144. In the embodiment shown, the plurality of light wavelengths 144 are UV wavelengths. In some embodiments, the UV wavelengths may be within a range of 285 nm-400 nm, although it may be preferable to have the UV wavelengths be UVA wavelengths within a range of 320 nm-370 nm.

Figure 2:
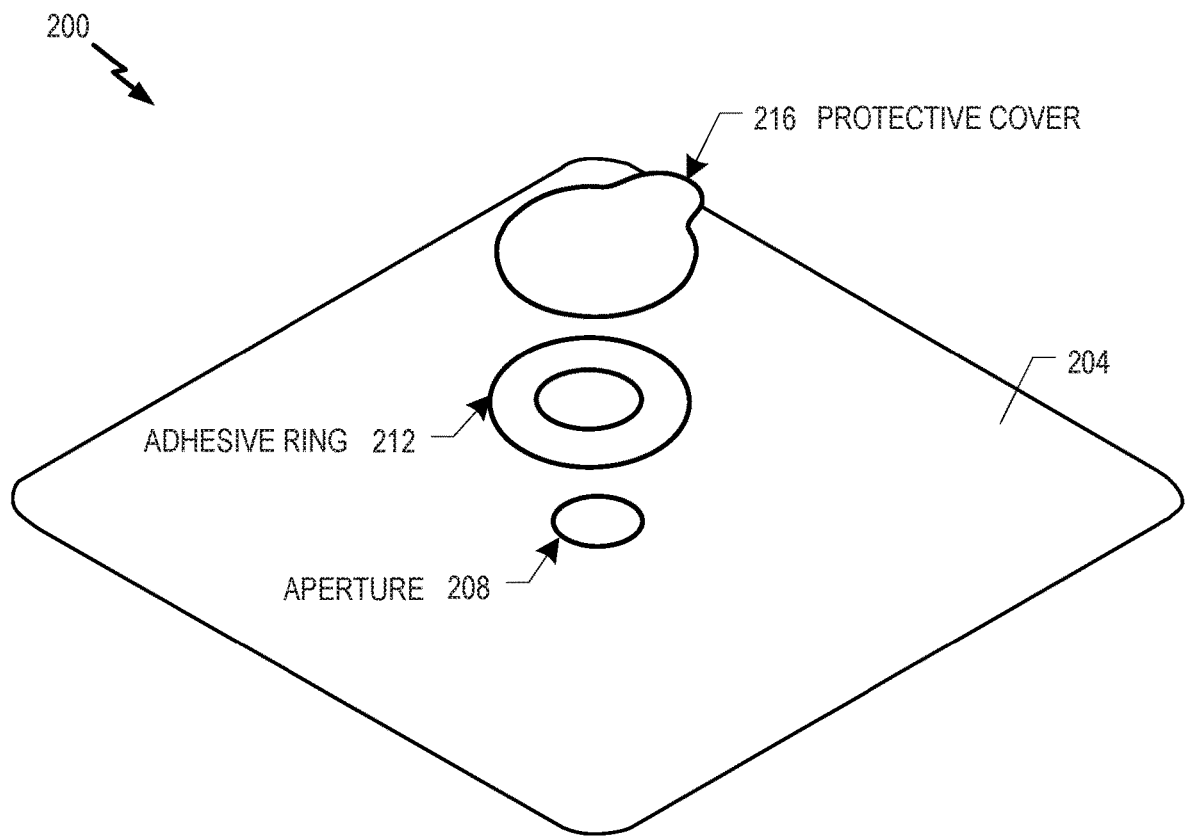
FIG. 2 is a diagram showing an exploded view of an exemplary adhesive dressing in accordance with an illustrative embodiment of the present disclosure.

FIG. 2 is a diagram showing an exploded view of an exemplary adhesive dressing 200 in accordance with an illustrative embodiment of the present disclosure. In the embodiment shown, dressing 200 includes an outer surface 204, an aperture 208 that passes through the dressing between the outer surface 204 and an inner surface applied to patient tissue, an adhesive ring 212, and a protective cover 216. In some embodiments, dressing 200 is applied to a patient tissue site with aperture 208 disposed over a treatment area. Adhesive ring 212 is a switchable adhesive disposed on the outer surface 204 around the edge, boundary, or circumference of aperture 208. Although aperture 208 is shown to be a round hole, aperture 208 can be a hole of a different shape. Likewise, adhesive ring 212 does not have to be a circular ring but can be any shape disposed around the boundary of aperture 212. In the embodiment shown, the adhesive exposure surface of adhesive ring 212 is covered by protective cover 216 and has an adhesive surface area large enough to attach to an adhesive receiving surface of a medical therapy unit. In the embodiment shown, protective cover 216 completely covers adhesive ring 212 to prevent premature exposure of the adhesive to deactivating wavelengths. In some embodiments, protective cover 216 can be a siliconized paper tab that can be peeled away before the medical therapy unit is applied to the dressing. When a medical therapy unit is desired to be attached to the dressing, protective cover 216 can be removed to expose the adhesive surface of adhesive ring 212 and attached the medical therapy device to the dressing via aperture 208. In some embodiments, outer surface 204, adhesive ring 212, and protective cover 216 can correspond to surface 104, adhesive layer 108, and blocking layer 112, respectively, shown in FIG. 1A. In some embodiments, the switchable adhesive of adhesive ring 212 can contain photo initiators (PI's) that are sensitive to the UVA wavelength range of 285-400 nm and, more specifically, 320-370 nm.

Figure 3:
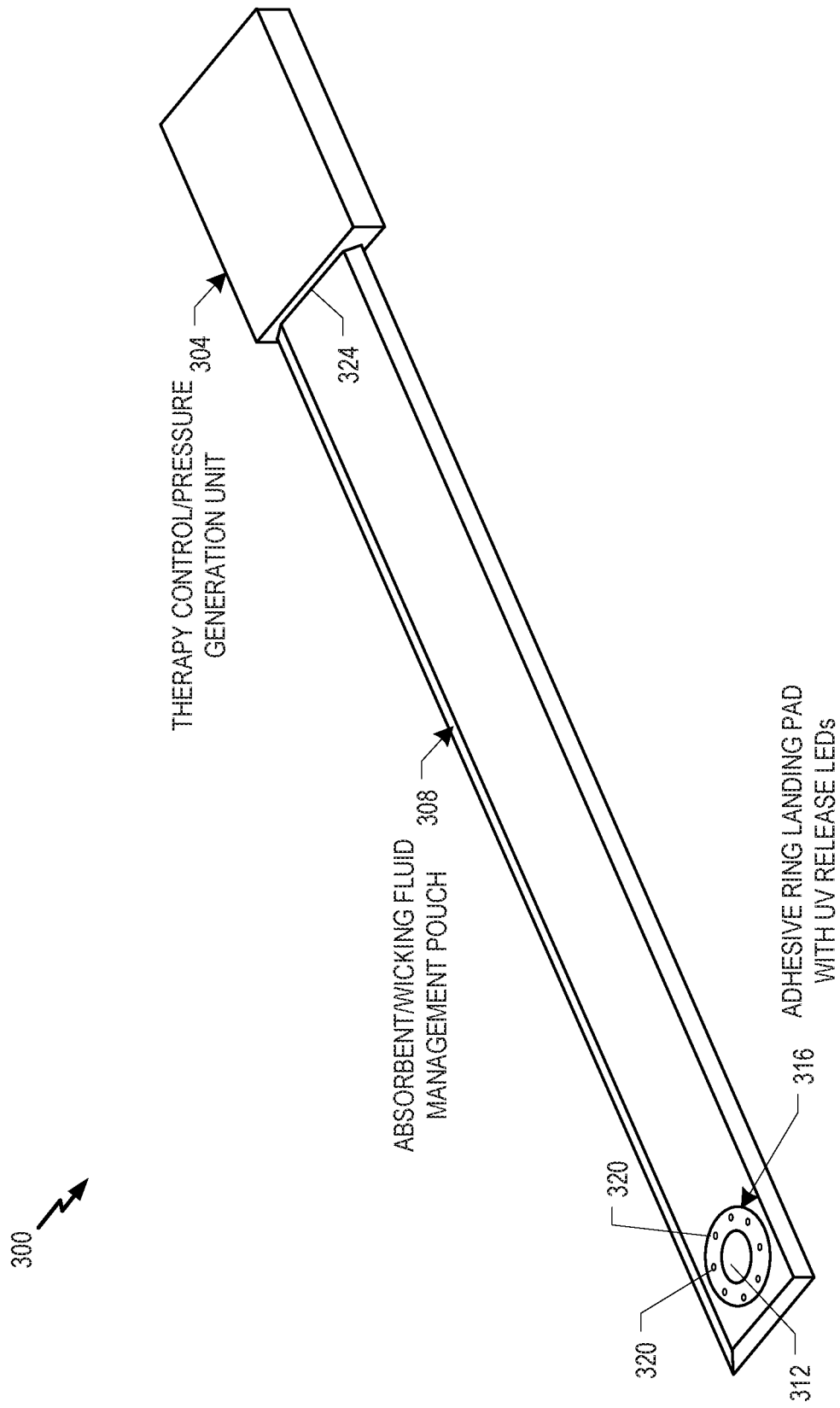
FIG. 3 is a diagram of an exemplary wearable NPWT medical fluid collection system 300 in accordance with an illustrative embodiment of the present disclosure.

FIG. 3 is a diagram of an exemplary wearable NPWT medical fluid collection system 300 in accordance with an illustrative embodiment of the present disclosure. In the embodiment shown, system 300 includes a therapy control/pressure generation unit 304, a flexible pouch 308, a connection aperture 312, an adhesive ring receiving area/landing pad 316, and a plurality of light sources 320. In the embodiment shown, flexible pouch 308 contains materials capable of absorbing and wicking wound fluids as well as allowing a communication of negative pressure from the therapy generation unit 304 to the connection aperture 312.

In the embodiment shown, therapy generation unit 304 is disposed at one end of flexible pouch 308 and connection aperture 312 is disposed at the opposite end of the pouch 308. Example absorbent materials that can be used with pouch 308 include Gelok® 300 gsm absorbent or Texsus® 800 gsm. In the embodiment shown, therapy generation unit 304 can contain a means to evacuate the system to a suitable level of negative pressure, a means to measure this pressure, and a control system capable of using these components to ensure that effective, safe therapy at the wound site can be maintained. At an interface 324 between the pouch 308 and the therapy generation unit 304, there can be be a filter designed to prevent the flow of liquids while allowing the transmission of gases. An example filter material can be Wm Gore® MMT 314.

In the embodiment shown, system 300 interfaces with dressing 200 at communication aperture 312 and adhesive receiving area 316. In the embodiment shown, adhesive receiving area 316 is disposed around the edge, boundary, or circumference of communication aperture 312. Adhesive receiving area 316 acts as a "landing pad" area designed to be a good location to mate the adhesive ring 212 of the dressing 200 to the fluid management system 300. Specifically, adhesive receiving area 316 receives the adhesive surface of adhesive ring 212 in a position where communication aperture 312 aligns with dressing aperture 204. In the embodiment shown, a plurality of light sources 320 are disposed around adhesive receiving area 316 and are powered by the control system. In some embodiments, a single light source can be used. In the embodiment shown, light sources 320 are UV frequency LEDs that are mounted into the adhesive receiving area 316 and disposed around the boundary of communication aperture 312. However, in some embodiments, other types of light sources (e.g., visible, infrared) can be used. In some embodiments, adhesive receiving area 316 can include the various apertures or passageways (denoted by lines 136 in FIG. 1C) discussed previously that allow certain wavelengths of light to pass through the adhesive receiving area 316 and impinge on adhesive ring 212. In some embodiments, adhesive receiving area 316 can completely cover the surface of adhesive ring 212 when coupled together to prevent exposure of the surface of adhesive ring 212 to ambient light that could possibly prematurely deactivate the switchable adhesive. In some embodiments, a filter layer can be disposed onto adhesive ring 212 configured to block at least a portion and or intensity of the plurality of light wavelengths that activate the adhesive release agent to deactivate the adhesive. For example, after protective layer 216 is removed, adhesive ring 212 may be briefly exposed to ambient light containing UVA wavelengths. As discussed above, if adhesive ring 212 is configured to be deactivated by UVA wavelengths, these wavelengths must be prevented from impinging upon adhesive ring 212 until a time when the adhesive is desired to be deactivated. Therefore, a filter layer can be disposed on the surface of adhesive ring 212 to block out a portion of these UVA wavelengths or a particular intensity of UVA wavelengths that exist in ambient light but allow a portion of UVA wavelengths or a higher intensity of UVA wavelengths from light sources to pass through.

In the embodiment shown, light sources 320 can switch between ON/OFF states based on corresponding signals received from the control system. In the embodiment shown, light sources 320 are OFF when system 300 is applied to dressing 200 and remain in an OFF state as long as the system 300 is desired to be coupled to dressing 300. When it is desired to separate system 300 from dressing 200, light sources 320 receive a control signal that switches them from an OFF to an ON state. In the ON state, light sources 320 emit a plurality of wavelengths that are configured to impinge on the adhesive layer and deactivate the switchable adhesive. In some embodiments, light sources 320 are controlled by a radiation source driver configured to receive an ON signal from a controller and turn the light sources 320 to an ON state In some embodiments, the control system includes at least one controller comprising at least one processor that can be controlled by a user of system 300. For example, a user can send inputs to the controller via one or more manual controls such as switches or buttons disposed on system 300. These manual controls can direct the controller to switch between the ON and OFF switching states of light sources 320. In other embodiments, the controller can be controlled automatically, such as via a system of sensors and computer-readable media having executable instructions for execution by the at least one processor of the controller. These sensors can include fluid level sensors, fluid pressure sensors, or other suitable sensors used with system 300. In these embodiments, light sources 320 may be automatically activated at a particular time, after a predetermined time period has elapsed, and/or based on control signals denoting that dressing 200, pouch 308, and/or therapy generation unit 304 needs to be replaced. In some embodiments, a light diffuser or light pipe may also be integrated with the light sources 320 or LED array to focus the plurality of emitted wavelengths onto the adhesive receiving area 316 to ensure an even and/or controlled exposure of the adhesive ring 212 sufficient to deactivate the adhesive. In some embodiments, the plurality of wavelengths are focused to expose the entire adhesive surface or to expose only certain parts of the surface that are intended to weaken the adhesive in prescribed places.

In some embodiments, the adhesive of adhesive ring 212 may be predisposed to crosslink/deactivate upon exposure to electromagnetic heating/deactivation means. In these embodiments, the adhesive may be comprised of metallic particles. In some embodiments, the particles are most preferably implemented as nanoferrites. Nanoferrites are iron oxide particles which have a large specific surface area and are super-paramagnetic. Nanoferrites designate ferrites which have a particle size of less than 30 nm. These particles enable the heating of the adhesive by absorbing energy from electromagnetic alternating fields and discharging the energy to the environment again as heat. Adhesive means, which are themselves only very poor microwave absorbents, can thus be inductively heated. In these embodiments, adhesive receiving area 316 can contain one or more electromagnetic sources that emit electromagnetic wavelengths instead of light sources 320 that emit light wavelengths. In these embodiments, the electromagnetic heating can induce a transient or flash heat response generating a local temperature greater than 60° C. temporarily in order to further crosslink the polymeric adhesive chain and thereby move the adhesive from a viscoelastic state to an elastic state. This action is similar to activation of release agents by particular light wavelengths. Therefore, all wavelengths which are usable for crosslinking/heating, in particular radiofrequency waves, ultraviolet waves, and microwaves, can be used to deactivate the switchable adhesive.

In some embodiments, adhesive ring 212 is designed to preferentially remain adhered to the dressing surface 204 upon removal of system 300 from dressing 200. After adhesive ring 212 has been deactivated and removed, a new adhesive ring can be placed on the dressing and used to re-adhere the system 300 to dressing 200 after all replacements have been made. In other embodiments, adhesive ring 212 is designed to preferentially adhere to the system 300 in situations where it is desirable to leave the dressing 200 in place and replace the system 300 more often that the dressing 200. For instance, this situation may arise when a NP system is applied to a VLU, graft or epithelial tissues where the dressing change interval is less than the NP system change interval.

In some embodiments, a further array of light sources or electromagnetic source and corresponding switchable adhesives may be used to separate the fluid storage pouch 308 from the therapy generation unit 304 at interface 324 to enable an easy separation between pouch 308 and therapy generation unit 304 in the event that pouch 308 and/or therapy generation unit 304 need to be changed or replaced. In these embodiments, the further array of sources can be activated as described above to deactivate the adhesive when detachment between two system elements is desired.

Figure 4:
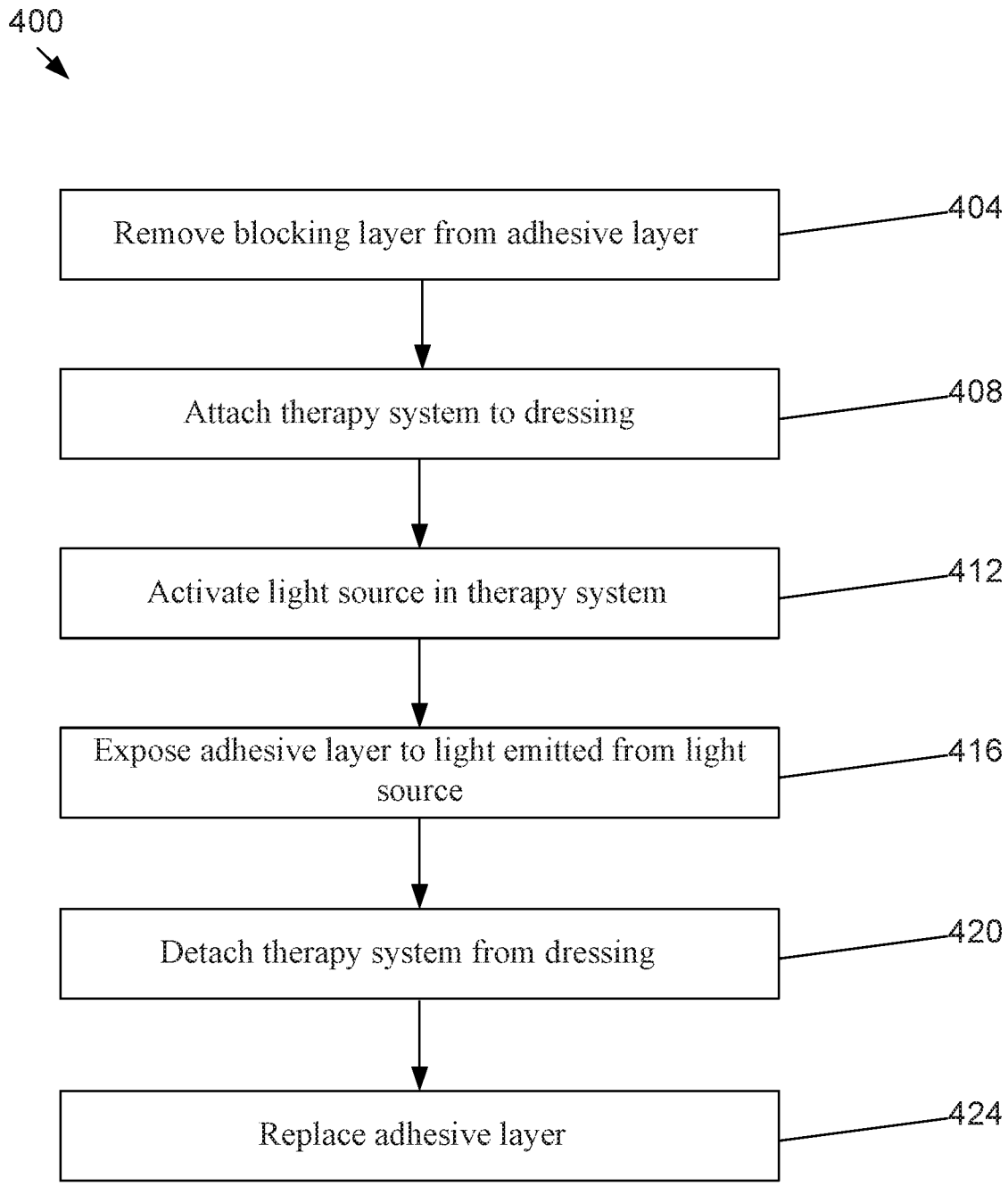
FIG. 4 is a flowchart illustrating a process for using the exemplary wearable NPWT medical fluid collection system shown in FIG. 3 with the dressing shown in FIG. 2 in accordance with an illustrative embodiment of the present disclosure.

FIG. 4 is a flowchart illustrating a process 400 for using the exemplary wearable NPWT medical fluid collection system 300 with the dressing 200 in accordance with an illustrative embodiment of the present disclosure. The process illustrated in FIG. 4 can be implemented by a user of system 300. The process begins by removing blocking layer 112 from adhesive layer 108 (step 404). In this step, the adhesive surface of adhesive layer 108 is exposed and can bind to the surface 120 of therapy system 300. In step 408, therapy system 300 can be attached to dressing 200 by applying switchable adhesive ring 212 to the adhesive receiving area 316 of the therapy system 300. When it is desired to detach therapy system 300 from dressing 200, light sources 320 can be activated by a controller at step 412. As discussed previously, this can be done either manually by a user actuating a switch or may be done automatically based on feedback received by a controller (e.g., signals from sensors and/or instructions from computer-readable media). Upon activation of light sources 320, the switchable adhesive ring 212 is exposed to the plurality of light wavelengths emitted from light sources 320 at step 416. The plurality of light wavelengths can stimulate release agents 124 to deactivate the adhesive and enable detachment of the therapy system 300 from the dressing 200 at step 420. At step 424, the deactivated adhesive ring 212 can be removed and replaced with a new, unused adhesive ring 212. In this way, the process 400 can be repeated.

The flowcharts and block diagrams in the different depicted embodiments illustrate the architecture, functionality, and operation of some possible implementations of the apparatus and methods. In some alternative implementations, the function or functions noted in the block can occur out of the order noted in the figures. For example, in some cases, two blocks shown in succession can be executed substantially concurrently, or the blocks can sometimes be executed in the reverse order, depending upon the functionality involved.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the disclosed methods, devices, and systems are not intended to be limited to the particular forms disclosed. Rather, they include all modifications and alternatives falling within the scope of the claims, and embodiments other than those shown may include some or all of the features of the depicted embodiment. For example, components may be combined as a unitary structure and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A radiation deactivated adhesive drape having an inner surface configured to be coupled to tissue and an outer, non-tissue facing surface, the radiation deactivated adhesive drape comprising:
a switchable adhesive disposed on the outer, non-tissue facing surface of the radiation deactivated adhesive drape the switchable adhesive being configured to adhere the radiation deactivated adhesive drape to a medical therapy unit, the switchable adhesive including:
a radiation-sensitive adhesive layer having at least one release agent disposed within the radiation-sensitive adhesive layer, wherein the at least one release agent is configured to weaken a bond of the radiation-sensitive adhesive layer to a surface upon exposure to at least one of a plurality of radiation wavelengths; and
a removable blocking layer having at least one blocking agent disposed within the removable blocking layer, wherein the removable blocking layer blocks the at least one of the plurality of radiation wavelengths from exposing the radiation-sensitive adhesive layer.

2. The radiation deactivated adhesive drape of claim 1, wherein the at least one of the plurality of radiation wavelengths are a plurality of electromagnetic wavelengths, and wherein the plurality of electromagnetic wavelengths include any one of ultraviolet (UV) light wavelengths between 280 nm and 400 nm, radio-frequency wavelengths, and microwaves.

3. The radiation deactivated adhesive drape of claim 2, wherein the at least one release agent is a photo initiator configured to deactivate the radiation-sensitive adhesive layer upon exposure to at least one of the plurality of electromagnetic wavelengths.

4. The radiation deactivated adhesive drape of claim 3, wherein the at least one release agent is a nanoferrite configured to deactivate the radiation-sensitive adhesive layer upon exposure to the at least one of the plurality of electromagnetic wavelengths.

5. The radiation deactivated adhesive drape of claim 4, wherein the nanoferrite is an iron oxide particle having a size of less than 30 nm and that is super-paramagnetic.

6. The radiation deactivated adhesive drape of claim 1, wherein the removable blocking layer is a peelable layer disposed on an outer surface of the radiation-sensitive adhesive layer and further comprising:
a filter layer configured to block at least a portion of the at least one of the plurality of radiation wavelengths that activate the at least one release agent, wherein the blocked portion of the at least one of the plurality of radiation wavelengths comprises one or more wavelengths below a wavelength intensity threshold; and an aperture disposed through the radiation deactivated adhesive drape configured to receive a portion of the medical therapy unit, wherein the switchable adhesive is disposed on the outer, non-tissue facing surface as an adhesive ring surrounding the aperture.

7. A medical therapy unit for medical fluid collection for attachment to a radiation deactivated adhesive drape, the medical therapy unit comprising:

an adhesive layer receiving area disposed on an outside surface of the medical therapy unit configured to allow a passage of at least one of a plurality of radiation wavelengths through the adhesive layer receiving area;

a radiation source disposed within the medical therapy unit adjacent to the adhesive layer receiving area and configured to emit the at least one of a plurality of radiation wavelengths; and a radiation source controller having at least one processor configured to control an ON/OFF state of the radiation source;

wherein the adhesive layer receiving area is configured to receive a switchable adhesive including a radiation-sensitive adhesive layer having at least one release agent disposed within the radiation-sensitive adhesive layer, wherein the at least one release agent is configured to weaken a bond of the radiation-sensitive adhesive layer to a surface upon exposure to the at least one of the plurality of radiation wavelengths, and further comprising:

a negative pressure generation unit configured to transmit one or more gasses within the medical therapy unit;

a flexible pouch having a first end coupled to the negative pressure generation unit and a second end coupled to the adhesive layer receiving area, wherein the flexible pouch is configured to enable passage of the one or more gasses and absorb and/or wick wound fluids; and a filter disposed at the second end of the flexible pouch.

8. The medical therapy unit of claim 7, wherein the radiation source is a light source, wherein the light source is an ultraviolet (UV) light source, wherein the at least one of a plurality of radiation wavelengths are a plurality of light wavelengths, and wherein the at least one of the plurality of light wavelengths are UV light wavelengths between 285 nm and 400 nm.

9. The medical therapy unit of claim 8, wherein the light source comprises one or more UV light emitting diodes (LEDs).

10. The medical therapy unit of claim 8, further comprising a light diffuser disposed between the light source and the adhesive layer receiving area and configured to focus the at least one of a plurality of light wavelengths to pass through the adhesive layer receiving area.

11. The medical therapy unit of claim 7, wherein the radiation source is an electromagnetic radiation source, wherein the plurality of radiation wavelengths are a plurality of electromagnetic wavelengths, and wherein the plurality of electromagnetic wavelengths include radio-frequency wavelengths or microwaves.

12. The medical therapy unit of any of claim 7, wherein the radiation source controller is configured to receive a radiation source activation signal and output an ON signal and further comprising a radiation source driver configured to receive the ON signal from the radiation source controller and place the radiation source in an ON state.

13. A method of operating a medical fluid collection system, the method comprising:

adhering a medical therapy unit to a drape having an inner surface configured to be coupled to tissue and an outer non-tissue facing surface, the adhering including:

removing a removable blocking layer from a radiation-sensitive adhesive layer disposed on the outer, non-tissue facing surface of the drape; and attaching the radiation-sensitive adhesive layer to an adhesive layer receiving area disposed on an outside surface of the medical therapy unit; and detaching the medical therapy unit from the drape, the detaching including:

activating a radiation source disposed within the medical therapy unit adjacent to the adhesive layer receiving area and configured to emit at least one of a plurality of radiation wavelengths;

exposing the radiation-sensitive adhesive layer to at least one of the plurality of radiation wavelengths, wherein the radiation-sensitive adhesive layer is deactivated upon exposure to the at least one of a plurality of radiation wavelengths; and removing the medical therapy unit from the drape.

14. The method of claim 13, wherein the adhesive layer receiving area disposed on an outside surface of the medical therapy unit is configured to allow a passage of at least one of a plurality of radiation wavelengths through the adhesive layer receiving area.

15. The method of claim 14, wherein the medical therapy unit further comprises:

a radiation source controller having at least one processor configured to control an ON/OFF state of the radiation source.

16. The method of claim 13, wherein the radiation-sensitive adhesive layer includes at least one release agent disposed within the radiation-sensitive adhesive layer, wherein the at least one release agent is configured to weaken a bond of the radiation-sensitive adhesive layer to a surface upon exposure to the at least one of the plurality of radiation wavelengths.

17. The method of claim 16, wherein the plurality of radiation wavelengths correspond to one of ultraviolet wavelengths, radio-frequency wavelengths, and microwave wavelengths.

18. The method of claim 16, wherein the at least one release agent disposed within the radiation-sensitive adhesive layer comprises a nanoferrite configured to deactivate the radiation-sensitive adhesive layer upon exposure to the at least one of the plurality of radiation wavelengths.

19. The method of claim 13, wherein an aperture disposed through the drape is configured to receive a portion of the medical therapy unit.

* * * * *